US008188087B2

(12) United States Patent
Reutzel-Eden et al.

(10) Patent No.: US 8,188,087 B2
(45) Date of Patent: May 29, 2012

(54) CRYSTALLINE (3-CYANO-1H-INDOL-7-YL)-[4-(4-FLUOROPHENETHYL)PIPERAZIN-1-YL]METHANONE PHOSPHATE

(75) Inventors: Susan Marie Reutzel-Eden, Zionsville, IN (US); Gregory Alan Stephenson, Fishers, IN (US)

(73) Assignee: Merck Patent GmbH, Darmstadt (DE)

( * ) Notice: Subject to any disclaimer, the term of this patent is extended or adjusted under 35 U.S.C. 154(b) by 604 days.

(21) Appl. No.: 12/299,554

(22) PCT Filed: Apr. 24, 2007

(86) PCT No.: PCT/US2007/067255
§ 371 (c)(1),
(2), (4) Date: May 1, 2009

(87) PCT Pub. No.: WO2007/130814
PCT Pub. Date: Nov. 15, 2007

(65) Prior Publication Data
US 2009/0221606 A1 Sep. 3, 2009

Related U.S. Application Data

(60) Provisional application No. 60/797,865, filed on May 5, 2006, provisional application No. 60/822,647, filed on Aug. 17, 2006.

(51) Int. Cl.
*A61K 31/497* (2006.01)
*A61K 31/44* (2006.01)
*A61K 31/41* (2006.01)
*A61K 31/425* (2006.01)
*C07D 237/26* (2006.01)
*C07D 401/12* (2006.01)
*C07D 403/12* (2006.01)
*C07D 413/12* (2006.01)

(52) U.S. Cl. ........... 514/254.09; 514/252.02; 514/252.7; 514/252.11; 514/252.19; 514/253.03; 544/233; 544/238; 544/284; 544/295; 544/296; 544/360; 544/363; 544/367; 544/373; 544/371

(58) Field of Classification Search ............. 514/254.09, 514/252.02, 252.7, 252.11, 252.19, 253.06; 544/233, 238, 284, 295, 296, 360, 363, 367, 544/373, 371
See application file for complete search history.

(56) References Cited

U.S. PATENT DOCUMENTS
6,838,461 B1 * 1/2005 Boettcher et al. ........ 514/254.09
2007/0259885 A1 11/2007 Bathe et al.

FOREIGN PATENT DOCUMENTS
WO   WO-01 07435 A   2/2001
WO   WO-02 059092 A  8/2002
WO   WO-2006 034774 A  4/2006

OTHER PUBLICATIONS

Reutzel-Edens, Susan M. et al., "Comprehensive Solid Form Screening and Physical Characterization of Prucanserin (2422347) Maleate and Phosphate Salts," PSR & D Technical Report, Sep. 14, 2005, pp. 1-43.
Diseroad et al., "Studies Conducted to Identify, Scale-up and Characterize Salts of LSN 2422347, Pruvanserin," PSR & D Technical Report, May 23, 2005, pp. 1-53.
International Search Report for PCT/US2007/067255 dated Jul. 31, 2007.

* cited by examiner

*Primary Examiner* — James O Wilson
*Assistant Examiner* — Ebenezer O Sackey
(74) *Attorney, Agent, or Firm* — Millen, White, Zelano & Branigan, P.C.

(57) ABSTRACT

The present invention relates to novel crystalline forms of (3-cyano-1H-indol-7-yl)-[4-(4-fluorophenethyl)piperazin-1-yl]methanone phosphate and to pharmaceutical compositions containing said forms.

19 Claims, No Drawings

CRYSTALLINE (3-CYANO-1H-INDOL-7-YL)-[4-(4-FLUOROPHENETHYL)PIPERAZIN-1-YL]METHANONE PHOSPHATE

This application claims the benefit of the filing date of U.S. Provisional Application Ser. Nos. 60/797,865 filed May 5, 2006 and No. 60/822,647 filed Aug. 17, 2006 which is incorporated by reference herein.

The present invention relates to novel crystalline forms of (3-cyano-1H-indol-7-yl)-[4-(4-fluorophenethyl)piperazin-1-yl]methanone phosphate, a pharmaceutical composition containing said forms, and a process of preparing said forms.

BACKGROUND OF THE INVENTION (3-cyano-1H-indol-7-yl)-[4-(4-fluorophenethyl)piperazin-1-yl]methanone (pruvanserin) is a highly selective $5\text{-HT}_{2A}$ receptor antagonist useful in treating a number of $5\text{-HT}_{2A}$ modulated disorders including depression and sleeping disorders, as described in WO 01/007435. Methods of preparing (3-cyano-1H-indol-7-yl)-[4-(4-fluorophenethyl)piperazin-1-yl]methanone and the hydrochloride salt are also disclosed therein. Further synthetic methods are described in WO 02/059092 and WO 05/009792.

Although (3-cyano-1H-indol-7-yl)-[4-(4-fluorophenethyl)piperazin-1-yl]-methanone is an effective pharmacological agent, the hydrochloride salt exhibits certain technical difficulties related to its polymorphic state. This salt's solid form converts from a single polymorphic form into a second, poorly crystalline, metastable polymorphic form upon compression during the manufacturing process. It is disadvantageous for a formulation to comprise a plurality of crystal forms of an active ingredient in that they may have different bioavailabilities and/or stability. Even slight variations in production conditions may compromise the reproducibility of the crystal form and therefore the performance of the formulated product. In addition, poorly crystalline materials are typically less desirable than highly crystalline materials because they are generally more difficult to handle during formulation processes.

Given the above, it is pharmacologically desirable and commercially advantageous to find a stable crystalline form that did not convert to other crystalline polymorphic forms during further processing, formulation and/or storage. Independently, it would be advantageous to find a crystalline form physically more conducive to formulation processing.

BRIEF SUMMARY OF THE INVENTION (3-Cyano-1H-indol-7-yl)-[4-(4-fluorophenethyl)piperazin-1-yl]methanone phosphate (hereinafter "the phosphate salt") has distinct advantages over the previously known hydrochloride salt form.

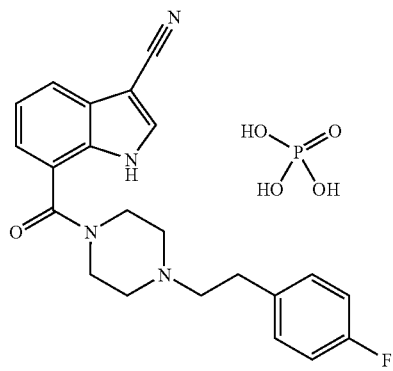

Two new crystalline forms are characterized by, inter alia, x-ray powder diffractometry, or alternatively, solid state nuclear magnetic resonance spectroscopy. One preferred embodiment of the present invention provides for a crystalline (3-cyano-1H-indol-7-yl)-[4-(4-fluorophenethyl)piperazin-1-yl]methanone phosphate hydrate Form I (Form I). Form I is characterized as a non-stoichiometric hydrate in that it retains water about 1.2% by weight of compound (up to approximately ⅓ mole of water per mole of compound) within the crystalline lattice when in equilibrium with a relative humidity of about 5% to about 95%.

A further embodiment of the invention provides for a crystalline (3-cyano-1H-indol-7-yl)-[4-(4-fluorophenethyl)piperazin-1-yl]methanone phosphate anhydrate (Anhydrate).

Additional embodiments of the present invention provide for pharmaceutical compositions comprising either Form I or the Anhydrate as an active ingredient in association with one or more pharmaceutically acceptable carriers, diluents or excipients.

DETAILED DESCRIPTION OF THE INVENTION

Crystalline forms of (3-cyano-1H-indol-7-yl)-[4-(4-fluorophenethyl)piperazin-1-yl]methanone phosphate hydrate Form I and (3-cyano-1H-indol-7-yl)-[4-(4-fluorophenethyl)piperazin-1-yl]methanone phosphate anhydrate may be obtained as described in the Examples. The crystal forms and solvates may be characterized by, inter alia, X-ray powder diffraction- and/or by solid state nuclear magnetic resonance spectroscopy (SSNMR) using techniques well known in the art, as for example but not limited to methods essentially as described below.

The invention also relates to pharmaceutical compositions comprising either Form I or Anhydrate as an active ingredient in association with one or more pharmaceutically acceptable carriers, diluents and/or excipients. These compositions can be administered by a variety of routes including oral, buccal, intranasal, transdermal, subcutaneous, intravenous, intramuscular, and pulmonary. Such pharmaceutical compositions and processes for preparing them are well known in the art See, e.g., Remington: The Science and Practice of Pharmacy (A. Gennaro, et al., eds., 19$^{th}$ ed., Mack Publishing Co., 1995).

The compositions are preferably formulated in a unit dosage form, each dosage containing from about 0.1 to about 500 mg, more usually about 5.0 to about 300 mg, of the active ingredient. The term "unit dosage form" refers to physically discrete units suitable as unitary dosages for subjects, each unit containing a predetermined quantity of active material calculated to produce the desired therapeutic effect, in association with at least one suitable pharmaceutically acceptable carrier, diluent and/or excipient.

Salt Synthesis and Crystallization

Synthetic methods to obtain (3-cyano-1H-indol-7-yl)-[4-(4-fluorophenethyl)-piperazin-1-yl]methanone are known in the art (see for example WO 01/07435, WO 02/059092 and WO 05/009792). The phosphate salt may be crystallized or subsequently re-crystallized employing a variety of crystallization methods. Generally, (3-cyano-1H-indol-7-yl)-[4-(4-fluorophenethyl)piperazin-1-yl]methanone may be added to a suitable reaction vessel with any pharmaceutically acceptable solvent at ambient temperature and stirred until the solid dissolves. If the solid does not dissolve, the mixture may be heated to a suitable temperature and/or additional solvent may be added to produce a homogeneous solution. Phosphoric acid, preferably between about 1.1 and about 1.5 equivalents, may then be added to the reaction mixture followed by stirring at a suitable temperature. After stirring for a suitable time and cooling to ambient temperature (if necessary), the crystalline solid may be isolated, as for example, by filtration and/or solvent removal. Suitable concentrations of phosphoric acid typically range from commercially available concentrate (approximately 86% by weight) to about 1 M in water or lower. Preferred concentrations of phosphoric acid are from about 1 M to about 2 M for ease of control of addition and crystallization.

Suitable solvents include, but are not limited to, methanol, ethanol, propan-1-ol, propan-2-ol, butan-2-ol, tetrahydrofuran, acetone, and the like. Suitable temperatures for salt formation typically range between about 50° C. to about 75° C. depending on the solvent. One preferred temperature range for salt formation is from the temperature at which the (3-cyano-1H-indol-7-yl)-[4-(4-fluorophenethyl)piperazin-1-yl] methanone is soluble up to the reflux temperature of the solvent. In principle, a solvent that does not totally dissolve (3-cyano-1H-indol-7-yl)-[4-(4-fluorophenethyl)piperazin-1-yl]methanone could be used. However, this may result in a slurry to slurry conversion of (3-cyano-1H-indol-7-yl)-[4-(4-fluorophenethyl)piperazin-1-yl]methanone to the salt.

Isolation temperatures typically range between about 5° C. and about 22° C. The salt has low solubility in all of the solvent systems tested, so this variable is deemed to have little impact on the yield or processing.

Example 1

Crystalline (3-cyano-1H-indol-7-yl)-[4-(4-fluorophenethyl)piperazin-1-yl]-methanone phosphate hydrate Form I Add (3-cyano-1H-indol-7-yl)-[4-(4-fluorophenethyl)piperazin-1-yl]methanone (300.0 g, 797 mmol.) and anhydrous ethanol (15 L, denatured with toluene) to a 22 L flask equipped with overhead agitation, heating mantle, and condenser. Heat the slurry to about 75° C. to provide a homogeneous solution. Add a solution of 1 M aqueous phosphoric acid (877 mL, 877 mmol, 1.1 equiv) over 10 minutes while maintaining the temperature above 72° C. The salt may begin precipitating after approximately 380 mL of phosphoric acid solution is added. Remove the heating mantle after the addition is complete, and allow the slurry to cool to about 22° C. Cool the slurry to about 5° C. and stir for about 2 hours. Filter the mixture and wash the cake three times with 500 mL cold ethanol. Dry the solid overnight in a vacuum oven at about 50° C. to provide 370 g (98% yield) of the title crystal form as a white solid.

Example 2

Crystalline (3-cyano-1H-indol-7-yl)-[4-(4-fluorophenethyl)piperazin-1-yl]-methanone phosphate hydrate Form I Add (3-cyano-1H-indol-7-yl)-[4-(4-fluorophenethyl)piperazin-1-yl]methanone (1.00 g, 2.66 mmol) and anhydrous ethanol (50 mL) to a flask equipped with a magnetic stir bar, heating mantle, and condenser. Heat the slurry to 65° C. to provide a homogeneous solution. Add a solution of 1 M aqueous phosphoric acid (4 mL, 4 mmol, 1.5 equiv) over 1 minute while maintaining the temperature above 60° C. Remove the heating mantle after the addition is complete, and allow the solution to cool to about 22° C. Precipitate may begin to form when the temperature reaches about 53° C. Stir the slurry for 2.5 hours at about 22° C. Filter the mixture and wash the cake with 5 mL, then 10 mL of ethanol. Dry the solid overnight in a vacuum oven at 50° C. to provide 1.23 g (98% yield) of the title crystal form as a white solid.

Example 3

Crystalline (3-cyano-1H-indol-7-yl)-[4-(4-fluorophenethyl)piperazin-1-yl]-methanone phosphate hydrate Form I Add (3-cyano-1H-indol-7-yl)-[4-(4-fluorophenethyl)piperazin-1-yl]methanone (12.00 g 31.9 mmol) and acetone (300 mL) to a 500 mL flask equipped with overhead agitation, heating mantle, and condenser. Heat the slurry to about 55° C. to provide a homogeneous solution. Add a solution of concentrated (86% by weight) phosphoric acid (4.00 g, 35.1 mmol, 1.1 equiv) over 1 minute. The salt may begin to precipitate after approximately half of the phosphoric acid is added. After the addition is complete, heat the mixture to about 55° C. for 2 hours. Remove the heating mantle and allow the slurry to cool to about 22° C. and then stir for 2 hours. Filter the mixture and wash the filter cake twice with 30 mL acetone. Dry the solid for 20 hours in a vacuum oven at about 50° C. to provide 14.15 g (93% yield) of the title crystal form as a white solid. Initially, this process may produce a precipitate that may be gummy, but may become granular upon further stirring.

Example 4

Crystalline (3-cyano-1H-indol-7-yl)-[4-(4-fluorophenethyl) piperazin-1-yl]-methanone phosphate hydrate Form I Combine (3-cyano-1H-indol-7-yl)-[4-(4-fluorophenethyl) piperazin-1-yl]-methanone (1.00 g, 2.66 mmol), acetone (10 mL) and dionized water (1.4 mL) and heat the slurry to about 55° C. to provide a homogeneous solution. Add 0.28 mL 1 M aqueous phosphoric acid followed by seed crystals of (3-cyano-1H-indol-7-yl)-[4-(4-fluorophenethyl)piperazin-1-yl]-methanone phosphate hydrate Form I (3.2 mg). Add an additional 2.22 mL 1 M aqueous phosphoric acid over 45 min. Allow the slurry to cool to room temperature and then stir for 2 h. Filter the mixture and wash the filter cake twice with 3 mL 35% (v/v) acetone/water and then 3 mL of 15% (v/v) acetone/water. Dry the solid for about 20 hours in a vacuum oven at 50° C. to provide 1.12 g (89% yield) of the title crystal form as a white solid.

Example 5

Crystalline (3-cyano-1H-indol-7-yl)-[4-(4-fluorophenethyl)piperazin-1-yl]methanone phosphate hydrate Form I Add 3 mL of 1 M aqueous phosphoric acid (3 mmol, 1.1 equiv) and 10 mL of tetrahydrofuran to a flask equipped with a magnetic stirring bar, heating mantle and condenser. Heat the solution to 60° C. Add dropwise 1.00 g (2.66 mmol) of (3-cyano-1H-indol-7-yl)-[4-(4-fluorophenethyl)piperazin-1-yl]methanone phosphate in 20 mL of tetrahydrofuran to the hot solution. The addition may be completed over 20 minutes while maintaining the temperature within a range of 58-60° C. Precipitate may form within 5 minutes after the addition is completed. The heating mantle may be removed and the slurry allowed to cool to ambient temperature, about 22° C., and stir for about 1.75 hours. Filter the solid, wash with 15 mL of tetrahydrofuran, and vacuum-dry at about 50° C. for 16 hours to yield 1.12 g (89% yield) of the title crystal form as a white solid.

Alternatively, crystalline (3-cyano-1H-indol-7-yl)-[4-(4-fluorophenethyl)piperazin-1-yl]methanone phosphate hydrate Form I may be prepared by standard recystallization techniques well known in the art. Suitable solvents for this process include but are not limited to aqueous butan-2-ol, acetic acid, methanol, ethanol, propan-1-ol, propan-2-ol, acetone, acetonitrile and the like.

Example 6

Crystalline (3-cyano-1H-indol-7-yl)-[4-(4-fluorophenethyl)piperazin-1-yl]-methanone phosphate anhydrate To a reaction vessel, slurry (3-cyano-1H-indol-7-yl)-[4-(4-fluorophenethyl)piperazin-1-yl]methanone phosphate (500 mg) in a mixture of acetic acid (2 mL) and DMSO (approximately 5 drops) at about 25° C. for about 4 days. The solid product may be isolated by vacuum filtration and air dried to produce 250 mg of the title crystal form.

The Anhydrate is stable under anhydrous conditions, but may be converted to Form I by exposure to water, including atmospheric humidity.

Conversely, hydrate Form I may be converted to the Anhydrate by dehydrating the solid at 0% RH and ambient temperature.

X-Ray Powder Diffraction

X-ray powder diffraction patterns may be obtained on a Siemens D-5000 X-ray powder diffractometer, equipped with a CuK$_\alpha$ source ($\lambda$=1.54056 Å) and a Kevex solid-state detector, operating at 40 kV and 50 mA, with 1 mm divergence and antiscatter slits, and a 0.1 mm detector slit. Each sample is scanned from 4° to 40° in 2θ, with a step size of 0.02° in 2° and a scan rate of ≧3 sec per step.

Alternatively, X-ray powder diffraction patterns may be obtained on a Bruker D4 Endeavor X-ray powder diffractometer with a Vantec detector, equipped with a CuK$_\alpha$ source ($\lambda$=1.54056 Å) operating at 40 kV and 50 mA. Each sample is scanned from 4° to 40° in 2θ, with a step size of 0.009° in 2θ.

It is understood that the diffraction patterns will vary slightly in 2θ and the relative intensity of the peaks as a function of relative humidity, as the crystal lattice dimensions vary with the absorption or loss of water. The error in 2θ should be reproducible to within 0.1 to 0.2 degrees. (See United States Pharmacopeia 23 National Formulary 18 Chapter "Physical Tests/X-ray Diffraction <941>", page 1843-1844, 1985.) Likewise, impurities within the sample may also have an effect on the pattern, including the reduction of the intensity of expected peaks, sometimes below the limits of detection, or the appearance of extraneous peaks which might overlap with (i.e. obscure) the expected peaks. As such, confirmation of a crystal form may be made based on any unique combination of distinguishing peaks, which are often but not always the more prominent peaks.

For the purposes of this disclosure, a "peak" in an X-ray powder diffraction pattern is taken to mean a diffraction peak having a relative intensity of at least 5% of the intensity of the strongest peak in the pattern. A "minor peak" will be understood to have a low intensity which may be less than 5% the intensity of the strongest peak observed for the diffraction pattern of the active pharmaceutical. A minor peak may be difficult to distinguish from background or variability due to differences in relative humidity and/or impurities in the crystals.

X-ray powder diffraction patterns are obtained for crystalline (3-cyano-1H-indol-7-yl)-[4-(4-fluorophenethyl)piperazin-1-yl]methanone phosphate hydrate Form I and for crystalline (3-cyano-1H-indol-7-yl)-[4-(4-fluorophenethyl)piperazin-1-yl]methanone phosphate anhydrate essentially as described above and are presented in Tables 1 and 2 below.

TABLE 1

X-ray powder diffraction peaks of greater than about 5% relative intensity for crystalline (3-cyano-1H-indol-7-yl)-[4-(4-fluorophenethyl)piperazin-1-yl]methanone phosphate hydrate Form I.

| 2θ | d Å | Relative % Intensity |
|---|---|---|
| 7.1 | 12.4 | 7.2 |
| 8.1 | 11.0 | 100.0 |
| 12.0 | 7.3 | 5.7 |
| 12.2 | 7.2 | 14.1 |
| 14.4 | 6.2 | 6.9 |
| 15.6 | 5.7 | 47.7 |
| 16.1 | 5.5 | 17.0 |
| 16.3 | 5.4 | 30.6 |
| 16.8 | 5.3 | 5.3 |
| 17.4 | 5.1 | 35.8 |
| 18.5 | 4.8 | 12.5 |
| 21.2 | 4.2 | 18.0 |
| 21.9 | 4.1 | 21.7 |
| 23.1 | 3.8 | 31.0 |
| 23.5 | 3.8 | 10.3 |
| 24.6 | 3.6 | 11.9 |
| 27.9 | 3.2 | 5.6 |

(Siemens D-5000 with CuK$_\alpha$ radiation source, $\lambda$ = 1.54056 Å)

TABLE 2

X-ray powder diffraction peaks of greater than about 5% relative intensity for crystalline (3-cyano-1H-indol-7-yl)-[4-(4-fluorophenethyl)piperazin-1-yl]methanone phosphate anhydrate.

| 2θ | d Å | Relative % Intensity |
|---|---|---|
| 7.2 | 12.27 | 19.3 |
| 8.0 | 11.02 | 100.0 |
| 8.1 | 10.87 | 12.9 |
| 12.5 | 7.08 | 29.3 |
| 15.4 | 5.76 | 6.6 |
| 15.8 | 5.60 | 14.6 |
| 16.1 | 5.51 | 39.0 |
| 16.8 | 5.28 | 6.8 |
| 17.3 | 5.11 | 24.9 |

TABLE 2-continued

X-ray powder diffraction peaks of greater than about 5% relative intensity for crystalline (3-cyano-1H-indol-7-yl)-[4-(4-fluorophenethyl)piperazin-1-yl]methanone phosphate anhydrate.

| 2θ | d Å | Relative % Intensity |
|---|---|---|
| 17.9 | 4.94 | 6.9 |
| 18.3 | 4.84 | 16.6 |
| 19.3 | 4.59 | 6.3 |
| 21.1 | 4.20 | 17.2 |
| 21.4 | 4.15 | 9.1 |
| 21.8 | 4.08 | 7.0 |
| 23.2 | 3.83 | 8.7 |
| 23.3 | 3.82 | 13.9 |
| 24.2 | 3.67 | 9.1 |
| 24.8 | 3.58 | 11.7 |
| 25.9 | 3.44 | 5.4 |

(Bruker D4 Endeavor with CuK$_\alpha$ radiation source, λ = 1.54056 Å)

The data show that Form I is characterized over the Anhydrate by a CuK$_\alpha$ radiation X-ray powder diffraction pattern having distinguishing peaks at 2θ values of 8.1 and 15.6. Alternatively, Form I is characterized by peaks at 2θ values of 8.1, 15.6 and 17.4. More specifically, Form I is characterized by peaks at 2θ values of 8.1, 15.6, 17.4 and 18.5. Yet more specifically, Form I is characterized by peaks at 2θ values of 8.1, 15.6, 17.4, 18.5 and 21.9. In addition to the above mentioned sets of peaks, or in the alternative, Form I's diffraction pattern is distinguished over the Anhydrate between 11 and 13 degrees 2θ by having a doublet of minor peaks at 2θ values of 12.0 and 12.2 where the anhydrate has widely divided peaks at 2θ values of about 11.7 (minor—not listed in table) and 12.5.

The Anhydrate is characterized by a CuK$_\alpha$ radiation X-ray powder diffraction pattern having distinguishing peaks at 2θ values of 8.0 and 12.5. Alternatively, the Anhydrate is characterized by peaks at 2θ values of 8.0, 12.5 and 18.3. More specifically, the Anhydrate is characterized by peaks at 2θ values of 8.0, 12.5, 18.3 and 15.8. Yet more specifically, the Anhydrate is characterized by peaks at 2θ values of 8.0, 12.5, 18.3, 15.8 and 23.3. In addition to the above mentioned sets of peaks, or in the alternative, the Anhydrate's diffraction pattern is distinguished over the hydrate Form I between 11 and 13 degrees 2θ by having widely divided peaks at 2θ values of about 11.7 (minor—not listed in table) and 12.5 where the hydrate Form I has a doublet of minor peaks at 2θ values of 12.0 and 12.2.

Solid State Nuclear Magnetic Resonance (SSNMR) Spectroscopy $^{13}$C and Cross polarization/magic angle spinning (CP/MAS) NMR (solid-state NMR or SSNMR) spectra may be obtained using a Varian Unity Inova™ 400 MHz NMR spectrometer operating at a carbon frequency of 100.578 MHz and equipped with a complete solids accessory and a Chemagnetics 4.0 mm T3 probe. The $^{13}$C acquisition parameters are as follows: 4.0 μs 90° proton r.f. pulse width, 62 kHz ramped-amplitude cross polarization (RAMP-CP), 3.0 ms contact time, 60 s pulse repetition time, 70 kHz TPPM decoupling, 8 kHz MAS frequency, 50 kHz spectral width, and 50 ms acquisition time. $^{13}$C chemical shifts are referenced to the methyl carbon resonance of hexamethylbenzene (δ=17.3 ppm) by sample replacement.

The solid state NMR spectrum for crystalline (3-cyano-1H-indol-7-yl)-[4-(4-fluorophenethyl)piperazin-1-yl]methanone phosphate hydrate Form I is obtained essentially as described above and the following chemical shifts are observed: (Peaks of greater than about 5% relative intensity) 30.6, 41.1, 46.2, 50.8, 55.3, 84.0, 115.0, 117.2, 119.4, 122.4, 128.7, 132.2, 133.6, 159.9, 162.4, and 166.8 ppm (std error+/−0.2 ppm).

Hydrate Form I is characterized by a SSNMR spectrum comprising distinguishing chemical shifts at 84.0-84.7+/−0.2 and 166.8-167.5+/−0.2 ppm. More specifically, Form I is characterized by a SSNMR spectrum comprising chemical shifts at 84.0-84.7+/−0.2, 166.8-167.5+/−0.2, and 159.8-160.7+/−0.2 ppm. Alternatively, Form I is characterized by a SSNMR spectrum comprising chemical shifts at 84.0-84.7+/−0.2, 166.8-167.5+/−0.2, and 30.6-31.3+/−0.2 ppm.

The Anhydrate is not stable under the conditions necessary for obtaining an SSNMR spectrum.

We claim:

1. A crystalline (3-cyano-1H-indol-7-yl)-[4-(4-fluorophenethyl)piperazin-1yl]methanone phosphate hydrate.

2. A crystalline (3-cyano-1H-indol-7-yl)-[4-(4-fluorophenethyl)piperazin-1yl]methanone phosphate hydrate Form I, characterized by a CuK$_\alpha$ radiation X-ray powder diffraction pattern comprising peaks at 2θ values of 8.1 and 15.6.

3. The crystalline (3-cyano-1H-indol-7-yl)-[4-(4-fluorophenethyl)piperazin-1yl]methanone phosphate hydrate Form I according to claim 2, characterized by a CuK$_\alpha$ radiation X-ray powder diffraction pattern comprising peaks at 2θ values of 8.1, 15.6 and 17.4.

4. The crystalline (3-cyano-1H-indol-7-yl)-[4-(4-fluorophenethyl)piperazin-1-yl]methanone phosphate hydrate Form I according to claim 2, characterized by a CuK$_\alpha$ radiation X-ray powder diffraction pattern comprising peaks at 2θ values of 8.1, 15.6, 17.4 and 18.5.

5. The crystalline (3-cyano-1H-indol-7-yl)-[4-(4-fluorophenethyl)piperazin-1yl]methanone phosphate hydrate Form I according to claim 2, characterized by a CuK$_\alpha$ radiation X-ray powder diffraction pattern comprising peaks at 2θ values of 8.1, 15.6, 17.4, 18.5 and 21.9.

6. The crystalline (3-cyano-1H-indol-7-yl)-[4-(4-fluorophenethyl)piperazin-1yl]methanone phosphate hydrate Form I according to claim 1, further characterized by a CuK$_\alpha$ radiation X-ray powder diffraction pattern comprising a doublet of peaks at 2θ values of 12.0 and 12.2.

7. The crystalline (3-cyano-1H-indol-7-yl)-[4-(4-fluorophenethyl)piperazin-1yl]methanone phosphate hydrate Form I according to claim 2, characterized by a solid state $^{13}$C nuclear magnetic resonance spectrum comprising chemical shift peaks at 84.0-84.7+/−0.2 and 166.8-167.5+/−0.2 ppm.

8. The crystalline (3-cyano-1H-indol-7-yl)-[4-(4-fluorophenethyl)piperazin-1yl]methanone phosphate hydrate Form I according to claim 2, characterized by solid state $^{13}$C nuclear magnetic resonance spectrum comprising chemical shift peaks at 84.0-84.7+/−0.2, 166.8-167.5+/−0.2, and 159.8-160.7+/−0.2 ppm.

9. A crystalline (3-cyano-1H-indol-7-yl)-[4-(4-fluorophenethyl)piperazin-1yl]methanone phosphate anhydrate.

10. The crystalline (3-cyano-1H-indol-7-yl)-[4-(4-fluorophenethyl)piperazin-1yl]methanone phosphate anhydrate according to claim 9, characterized by a CuK$_\alpha$ radiation X-ray powder diffraction pattern comprising peaks at 2θ values of 8.0 and 12.5.

11. The crystalline (3-cyano-1H-indol-7-yl)-[4-(4-fluorophenethyl)piperazin-1yl]methanone phosphate anhydrate according to claim 9, characterized by a CuK$_\alpha$ radiation X-ray powder diffraction pattern comprising peaks at 2θ values of 8.0, 12.5, and 18.3.

12. The crystalline (3-cyano-1H-indol-7-yl)-[4-(4-fluorophenethyl)piperazin-1-yl]methanone phosphate anhydrate according to claim 9, characterized by a CuK$_\alpha$ radiation X-ray powder diffraction pattern comprising peaks at 2θ values of 8.0, 12.5, 18.3, and 15.8.

13. The crystalline (3-cyano-1H-indol-7-yl)-[4-(4-fluorophenethyl)piperazin-1-yl]methanone phosphate anhydrate according to claim 9, characterized by a CuK$_\alpha$ radiation X-ray powder diffraction pattern comprising peaks at 2θ values of 8.0, 12.5, 18.3, 15.8, and 23.3.

14. A composition comprising crystalline (3-cyano-1H-indol-7-yl)-[4-(4-fluorophenethyl)piperazin-1-yl]methanone phosphate according to claim 1 as an active ingredient in association with a pharmaceutically acceptable carrier, diluent or excipient.

15. A pharmaceutical composition in unit dosage form comprising between approximately 0.1 and 500 mg of crystalline (3-cyano-1H-indol-7-yl)-[4-(4-fluorophenethyl)piperazin-1-yl]methanone phosphate hydrate according to claim 1 as an active ingredient in association with a pharmaceutically acceptable carrier, diluent or excipient.

16. A pharmaceutical composition in unit dosage form comprising between approximately 5.0 and 300 mg of crystalline (3-cyano-1H-indol-7-yl)-[4-(4-fluorophenethyl)piperazin-1-yl]methanone phosphate according to claim 1 as an active ingredient in association with a pharmaceutically acceptable carrier, diluent or excipient.

17. A composition comprising crystalline (3-cyano-1H-indol-7-yl)-[4-(4-fluorophenethyl)piperazin-1-yl]methanone phosphate hydrate Form I according to claim 2 as an active ingredient in association with a pharmaceutically acceptable carrier, diluent or excipient.

18. A composition comprising crystalline (3-cyano-1H-indol-7-yl)-[4-(4-fluorophenethyl)piperazin-1yl]methanone phosphate anhydrate according to claim 9 as an active ingredient in association with a pharmaceutically acceptable carrier, diluent or excipient.

19. A composition comprising crystalline (3-cyano-1H-indol-7-yl)-[4-(4-fluorophenethyl)piperazin-1yl]methanone phosphate anhydrate according to claim 10 as an active ingredient in association with a pharmaceutically acceptable carrier, diluent or excipient.

* * * * *